(12) United States Patent
Barne et al.

(10) Patent No.: US 11,278,480 B2
(45) Date of Patent: Mar. 22, 2022

(54) ANTIMICROBIAL COMPOSITION COMPRISING A FATTY ACID/SOAP/POLYVINYL ALCOHOL MIXTURE

(71) Applicant: Conopco, Inc., Trumbull, CT (US)

(72) Inventors: Sameer Keshav Barne, Pune (IN); Maya Treesa Saji, Bangalore (IN)

(73) Assignee: CONOPCO, INC., Englewood Cliffs, NJ (US)

( * ) Notice: Subject to any disclaimer, the term of this patent is extended or adjusted under 35 U.S.C. 154(b) by 30 days.

(21) Appl. No.: 16/638,588

(22) PCT Filed: Aug. 2, 2018

(86) PCT No.: PCT/EP2018/071043
§ 371 (c)(1),
(2) Date: Feb. 12, 2020

(87) PCT Pub. No.: WO2019/038049
PCT Pub. Date: Feb. 28, 2019

(65) Prior Publication Data
US 2020/0246235 A1 Aug. 6, 2020

(30) Foreign Application Priority Data
Aug. 25, 2017 (EP) .................................... 17187899

(51) Int. Cl.
| C11D 17/08 | (2006.01) |
| A61K 8/36 | (2006.01) |
| A61K 8/46 | (2006.01) |
| A61K 8/81 | (2006.01) |
| A61Q 19/10 | (2006.01) |

(52) U.S. Cl.
CPC ................ *A61K 8/361* (2013.01); *A61K 8/36* (2013.01); *A61K 8/463* (2013.01); *A61K 8/8129* (2013.01); *A61Q 19/10* (2013.01)

(58) Field of Classification Search
CPC .... C11D 1/20; C11D 1/37; C11D 1/12; C11D 1/29; C11D 3/042; C11D 3/2079; C11D 3/3753; C11D 3/48; C11D 9/007; C11D 9/02; C11D 17/08
See application file for complete search history.

(56) References Cited

U.S. PATENT DOCUMENTS

| 3,050,467 | A | 8/1962 | Horowtiz et al. | |
| 6,436,444 | B1 | 8/2002 | Richter et al. | |
| 6,495,136 | B1* | 12/2002 | Weisgerber | C11D 3/386 424/94.64 |
| 6,627,586 | B1* | 9/2003 | Brooks | A61K 8/345 510/130 |
| 7,109,241 | B1 | 9/2006 | Richter et al. | |
| 2005/0142090 | A1* | 6/2005 | Watanabe | A61K 8/442 424/70.9 |
| 2006/0094628 | A1* | 5/2006 | Wei | A61K 8/0237 510/417 |
| 2007/0020365 | A1 | 1/2007 | Herdt et al. | |
| 2008/0014247 | A1 | 1/2008 | Lu et al. | |
| 2010/0234328 | A1 | 9/2010 | Ahmed et al. | |
| 2012/0220510 | A1* | 8/2012 | Clapp | A61K 8/0295 510/159 |
| 2013/0224125 | A1 | 8/2013 | Kolazi et al. | |
| 2014/0289969 | A1* | 10/2014 | Sadlowski | C11D 1/29 8/137 |
| 2014/0349902 | A1* | 11/2014 | Allef | A61K 8/361 510/119 |
| 2015/0105313 | A1* | 4/2015 | Meier | C11D 17/043 510/406 |
| 2015/0272969 | A1* | 10/2015 | Ahmed | A61K 31/60 514/159 |
| 2016/0362646 | A1* | 12/2016 | Agarkhed | C11D 3/48 |

FOREIGN PATENT DOCUMENTS

| CN | 103766329 | 5/2014 |
| WO | WO9221238 | 10/1992 |
| WO | WO9221238 | 12/1992 |
| WO | WO0013506 | 3/2000 |

OTHER PUBLICATIONS

Search Report and Written Opinion in PCTEP2018071043; dated Oct. 1, 2018.
Search Report and Written Opinion in EP17187899; dated Oct. 20, 2017.
IPRP2 in PCTEP2018071043; dated Aug. 9, 2019.
Search Report and Written Opinion in PCTEP2018071043; dated Oct. 1, 2018; World Intellectual Property Org. (WIPO).

* cited by examiner

*Primary Examiner* — Charles I Boyer
(74) *Attorney, Agent, or Firm* — Krista A. Kostiew

(57) ABSTRACT

The present invention relates to an antimicrobial composition at the pH of the skin. Particularly, it relates to an antimicrobial composition comprising water soluble vinyl polymer, a carboxylic acid having pKa greater than 4.5; and an anionic surfactant, wherein the composition has pH in the range 4.5 to 6.5. The compositions provides synergistic antimicrobial effect in relatively shorter contact time. The invention further relates to a method of disinfecting a surface using the composition.

17 Claims, No Drawings

ANTIMICROBIAL COMPOSITION COMPRISING A FATTY ACID/SOAP/POLYVINYL ALCOHOL MIXTURE

CROSS REFERENCE TO RELATED APPLICATIONS

The present application is a U.S. National Phase Application under 35 U.S.C. § 371 of International Application No. PCT/EP2018/071043, filed on Aug. 2, 2018, which claims priority to European Patent Application No. 17187899.4, filed on Aug. 25, 2017, the contents of which are incorporated herein in their entireties.

FIELD OF THE INVENTION

The present invention relates to an antimicrobial composition and more particularly to an antimicrobial composition at the pH of skin.

BACKGROUND OF THE INVENTION

People try to take good care of the external surfaces of their body as well as those of their pets to enable overall good health. Specific skin related issues that people care about include, good skin health free of infections, good skin tone and adequate moisturization. Oral cavity is another external surface that people try to take active care to maintain. They prefer their oral cavity including the gums and teeth to be free of problems like cavities, tartar, gingivitis, caries, bad breath also known as halitosis and plaque. Typically, people are also concerned with hair and scalp care. They generally prefer to have thick and long hair with minimum hair fall. Dandruff is a commonly occurring scalp problem for which a fungal microorganism has been implicated.

A good health for external surfaces including skin, oral cavity and scalp care are typically achieved by keeping them free of infections. One way to tackle infections is to treat it using antimicrobials after the infection has set in. Another approach is to leave a minimal amount of antimicrobial composition on the surface like e.g. skin of the hands, so that any invading microorganisms like e.g. bacteria are killed or inactivated so as to minimize spread of disease. Some bacteria like *Escherichia coli* (*E. coli*) and *Staphylococcus aureus* (*S. aureus*) are commonly found on the human skin. These bacteria per se do not trigger a pathogenic effect whilst commonly present on the skin. However, when they enter the human body through cuts on the skin and through acts like ingestion, these bacteria become pathogenic. Therefore, keeping the external surface of the body like e.g. hand and scalp, free of bacteria helps in preventing them from entering the human body thereby achieving the desired hygiene.

Various germicidal compositions are disclosed that may be applied on to the skin of humans or warm-blooded animals. Some of these also discloses antimicrobial composition with polymers and carboxylic acids.

WO 00/13506 A2 (Alcide Corp.) discloses a freeze-resistance topical germicide for application to skin, such as the teats of a dairy cow. The germicide may be a one-part composition or a two-part system. The one-part disinfecting composition comprises an organic acid germicide and a non-esterifying antifreeze. The two-part system comprises a first part and a second part adapted to be mixed to yield the disinfecting composition. The first part comprises a metal chloride and a chlorite-stable antifreeze, and the second part comprises an organic acid germicide and a non-esterifying antifreeze, or an inorganic acid and either an alcohol or a non-esterifying antifreeze.

U.S. Pat. No. 6,436,444 (Ecolab Inc) discloses a mastitis control composition which comprises an aliphatic carboxylic acid having a chain length C6 to C12, an organic film forming agent e.g. PVA and polyvinyl acetate, rheology modifying material, an emollient, a surfactant and a buffer, and a chloride dioxide generating chemical such as sodium chlorite dissolved in an aqueous carrier. The base formulation in examples of U.S. Pat. No. 6,436,444 comprises carboxylic acid, such as nonanoic acid, octanoic acid, decanoic acid, a mixture of octanoic acid and decanoic aid and heptanoic acid, and PVA. To said base formulation an aqueous solution of sodium chlorite is added and pH of some of the compositions exemplified therein is less than 3.

U.S. Pat. No. 7,109,241 (Ecolab, Inc.) discloses an antimicrobial composition that can be used as a teat dip for milk producing animals. At least some embodiments of invention disclosed therein provide superior antimicrobial protection against mastitis causing organisms. The composition comprises a fatty acid containing 6 to 12 carbon atoms like e.g. heptanoic acid and a carrier medium including a freezing point depressant component. The compositions may further include rheology modifiers like e.g. hydroxyethyl cellulose, carboxymethyl cellulose, polyacrylic acid (PAA) and polyvinyl pyrrolidone (PVP), to enhance viscosity or thicken the composition.

US2010/0234328 (Delaval Holdings) discloses an antimicrobial composition comprising an organic acid and an anionic surfactant. It relates to topical application of the composition on an animal. It also relates to a method of using an antimicrobial composition comprising organic acid and an anionic surfactant to reduce microbial concentrations that may relate to treatment or prevention of mastitis. Several examples of organic acids like e.g. lactic acid, salicylic acid, citric acid, hexanoic acid and octanoic acid, are disclosed. The composition may further comprise additives like barrier forming agents like e.g. hydroxyethyl cellulose, sodium alginate, xanthan gum, polyvinyl alcohol (PVA) and PVP.

US2013/224125 (Kolazi et al.) discloses a non-alcoholic or slightly alcoholic antibacterial mouthwash composition with improved antimicrobial efficacy wherein the composition comprises a water soluble matrix composite made of a water soluble polymer like PVP and a water soluble surfactant, at least one water immiscible or water insoluble antibacterial agent and optionally a weak carboxylic acid like e.g. citric acid, tartaric acid, lactic acid, benzoic acid and combinations thereof.

Various routes for improving the biocidal activity of soap based cleansing compositions have been suggested.

US2008014247A (Lu et al., 2008) discloses a composition having metal containing material, stearic acid and a pharmaceutically acceptable carrier to treat conditions caused by gram-positive, gram-negative, fungal pathogens and/or antibiotic-resistant bacteria. It further provides a method for inhibiting biofilm proliferation. The metal containing material can be silver.

U.S. Pat. No. 3,050,467 B1 (Horowitz et al. 1962) discloses an antimicrobial cleansing composition consisting essentially of a mixture of a water-soluble soap and a silver salt of partially depolymerized alginic acid. The composition provides synergestic antimicrobial activity.

However, addition of soap invariably increases the pH of the composition. High pH composition is harsh on the skin.

Consumer also has a preference to use a formulation with pH close to that of human skin. Another problem is, most of the soap based antimicrobial compositions has to be applied for sufficiently long time to get the antimicrobial benefit. However most of the people especially kids do not wash their hand/skin for long enough.

Carboxylic acids are one of the known compounds used as antimicrobials. One of the preferred ways consumers make use of antimicrobial compositions is through personal washing and cleansing compositions that provide antimicrobial benefit. Consumers tend to prefer such personal washing and cleansing compositions which tend to provide high amount of foam as they tend to associate the amount of foam generated with efficacy of such compositions. For the above reasons surfactants, especially anionic surfactant, is often included in such compositions. We have found that antimicrobial efficacy of carboxylic acids substantially reduced in presence of anionic surfactants.

Thus, on one hand, desired amount of foam is obtained because of presence of surfactant but on the other hand antimicrobial benefit of carboxylic acid gets affected at least partially, which is not preferred.

Hence, there is a need to provide an antimicrobial composition that provides improved antimicrobial effect in presence of anionic surfactant and provides such effect at skin pH (pH 4.5 to 6.5) at relatively short contact time.

It is therefore an object of the present invention to provide an antimicrobial composition.

It is yet another object of the present invention to provide an antimicrobial composition at the pH close to that of human skin.

It is a further object of the present invention to provide an antimicrobial composition with the ability to provide the antimicrobial benefit at relatively short contact time.

It is yet a further object of the present invention to provide an antimicrobial composition comprising carboxylic acids that provides improved antimicrobial effect in presence of anionic surfactant, and at the pH close to that of human skin.

The present inventors have surprisingly found that addition of low amount of a water soluble vinyl polymer comprising polyvinyl alcohol with a carboxylic acid having pKa greater than 4.5 provides synergistic antimicrobial activity in presence of an anionic surfactant, at relatively short contact time, thereby stratifying one or more of the above mentioned object.

SUMMARY OF THE INVENTION

In a first aspect, the invention relates to an antimicrobial composition comprising:
  a. 0.01 to 10% by weight of a water soluble vinyl polymer comprising polyvinyl alcohol,
  b. 0.1 to 20% by weight of a carboxylic acid having pKa greater than 4.5; and
  c. 1 to 80% by weight an anionic surfactant;
  wherein the pH of the composition is in the range of 4.5 to 6.5.

In a second aspect, the invention relates to a method of cleaning or disinfecting a surface comprising a step of applying on to the said surface a composition of the first aspect.

These and other aspects, features and advantages will become apparent to those of ordinary skill in the art from a reading of the following detailed description and the appended claims. For avoidance of doubt, any feature of one aspect of the present invention may be utilized in any other aspect of the invention. The word "comprising" is intended to mean "including" but not necessarily "consisting of" or "composed of". In other words, the listed steps or options need not be exhaustive. It is noted that the examples given in the description below are intended to clarify the invention and are not intended to limit the invention to those examples per se. Similarly, all percentages are weight/weight percentages unless otherwise indicated. Except in the operating and comparative examples, or where otherwise explicitly indicated, all numbers in this description indicating amounts of material or conditions of reaction, physical properties of materials and/or use are to be understood as modified by the word "about". Unless specified otherwise, numerical ranges expressed in the format "from x to y" are understood to include x and y. When for a specific feature multiple preferred ranges are described in the format "from x to y", it is understood that all ranges combining the different endpoints are also contemplated.

DETAILED DESCRIPTION OF THE INVENTION

Antimicrobial composition as mentioned herein above preferably means any composition, which is capable of killing or at least cause substantial reduction of the common disease causing microbes. The common disease causing gram-positive organisms includes *Staphylococcus, Streptococcus* and *Enterococcus* spp. Some of common disease causing gram-negative organisms includes *Escherichia coli, Salmonella, Klebsiella* and *Shigella. Escherichia coli* and *Salmonella* can cause severe gastrointestinal illnesses.

The present invention provides an antimicrobial composition comprising water soluble vinyl polymers comprising polyvinyl alcohol, a carboxylic acid having pKa greater than 4.5 and an anionic surfactant wherein the pH of the composition is in the range of 4.5 to 6.5. Various components of the antimicrobial composition are described below. The compositions of the present invention are preferred for non-therapeutic use. More particularly, the compositions are preferred for use in obtaining antimicrobial effect when applied to surfaces of the human body that includes skin, hair or oral cavity. The most preferred use of the composition of the present invention on human skin, scalp or oral surface. The compositions may also be preferably used for hard surface cleaning applications.

Water Soluble Vinyl Polymer

The composition comprises a water soluble vinyl polymer comprising polyvinyl alcohol. Water soluble vinyl polymers are known to be used as thickeners, viscosity modifying agents and complex forming agents when used with ingredients like surfactants.

The water soluble vinyl polymer for the purpose of the present invention comprises polyvinyl alcohol. The most preferred water soluble vinyl polymer is polyvinyl alcohol.

The composition comprises from 0.01 to 10%, preferably from 0.05 to 8%, more preferably from 0.1 to 6%, even more preferably from 0.5 to 5%, further more preferably from 0.5 to 4%, still more preferably from 0.5 to 3%, even more preferably from 0.5 to 2% and most preferably 0.5 to 1.5% by weight of a water soluble vinyl polymer comprising polyvinyl alcohol.

Carboxylic Acid:

The composition of the present invention also comprises 0.1 to 20%, preferably 0.1 to 15%, more preferably 0.2 to 10% and most preferably 0.2 to 5% by weight of a carboxylic acid with $pK_a$ value greater than 4.5 or its derivatives thereof.

Carboxylic acids are organic acids having (—COOH) group as a part of their structure. An acid dissociation constant ($K_a$) represents the strength of an acid in a solution. The negative logarithm of $K_a$ is represented by pKa, which is quite relevant for practical applications of $K_a$.

$$pK_a = -\mathrm{logic}_{10} K_a$$

The higher the value of $pK_a$, the lower the extent of dissociation at a given pH. This is governed by the well-known Henderson-Hasselbalch equation.

According to the present invention the carboxylic acid having $pK_a$ greater than 4.5, more preferably greater than 4.6 and most preferably greater than 4.7.

Preferably, the range of $pK_a$ is in between 4.5 to 7, more preferably in between 4.5 to 6.5, and most preferably 4.5 to 6.

Preferably, the carboxylic acid is selected from fatty acid having chain length $C_4$ to $C_{12}$, more preferably $C_6$ to $C_{10}$ and most preferably from $C_6$ to $C_8$. The carboxylic acids are preferably selected from linear or branched aliphatic carboxylic acids, cyclic aliphatic carboxylic acids and mixtures thereof. Substituted Carboxylic acid with the above defined pKa range may also be preferably used. The most preferred substitution are methyl and/or ethyl.

The most preferred aliphatic carboxylic acids are selected from hexanoic acid (pKa: 4.88), cyclohexanoic acid (pKa: 4.91), 2-ethyl hexanoic acid (pKa: 4.72), octanoic acid (pKa: 4.89), 4-methyl octanoic acid (pKa: 4.93) and mixtures thereof.

Anionic Surfactant:

The composition of the present invention also comprises an anionic surfactant.

Preferred anionic surfactants include alkyl ether sulfate and sulfonates, alkyl sulfates and sulfonates, alkylbenzene sulfonates, alkyl and dialkyl sulfosuccinates, C8-C20 acyl isethionates, acyl glutamates, C8-C20 alkyl ether phosphates and mixtures thereof.

The most preferred anionic surfactants are selected from Sodium lauryl sulfate, Sodium lauryl ether sulfate.

The composition comprises from 1 to 80%, preferably from 5 to 75%, more preferably from 10 to 70% and even more preferably from 15 to 65% by weight of a surfactant.

One of the objective of the present invention is to provide a composition at skin pH. Therefore, pH of the composition of the present invention is preferably in the range of 4.5 to 6.5, more preferably 4.5 to 6 and most preferably about 5 to 6.

The composition of the present invention is a synergistic antimicrobial composition. The synergy effects is observed by combining 0.01 to 10% by weight of a water soluble vinyl polymer comprising polyvinyl alcohol and 0.1 to 20% by weight of a carboxylic acid having pKa greater than 4.5 or derivatives thereof in presence of an anionic surfactant. The inventors have found that addition of a low amount of a water soluble vinyl polymer comprising polyvinyl alcohol to a composition comprising carboxylic acids having pKa greater than 4.5 and an anionic surfactant provides improved antimicrobial effect, whereas the antimicrobial efficacy of carboxylic acids having pKa greater than 4.5 is substantially reduced in presence of an anionic surfactant. Moreover, such antimicrobial effect is obtained in relatively short contact times and at a pH close to that of human skin (pH 4.5 to 6.5). Such antimicrobial effect is especially important in a wash off processes where the contact time of the antimicrobial actives with the surface is low like e.g. preferably less than 5 minutes, more preferably less than 2 minutes, even more preferably less than a minute, further more preferably less than 45 seconds and still more preferably less than 30 seconds.

The synergistic antimicrobial composition of the present invention also comprises a cosmetically acceptable base. The base formulation may be varied depends on the kinds of application.

The composition of the present invention preferably in the form of a leave-on composition. The leave-on composition may be in the form of vanishing cream or may be in the form of a sanitizer composition. The most preferred application being the hand sanitization.

The antimicrobial composition may be in the form of a wipe, i.e. an antimicrobial wipe.

The cosmetically acceptable base is preferably a cream, lotion, gel or emulsion.

Personal care compositions (leave-on) may be prepared using different cosmetically acceptable emulsifying or non-emulsifying systems and vehicles. A highly suitable base is a cream. Vanishing creams are especially preferred. Tough it is not preferred to have soap in the composition of the present invention. However, a small amount soap which does not make the pH of the overall formulation greater than 7.5 is also within the scope of the present invention. Vanishing cream bases generally comprise 5 to 25% fatty acid and 0.1 to 10% soap. Vanishing cream base gives a highly appreciated matte feel to the skin. C13 to C20 fatty acids are especially preferred in vanishing cream bases, further more preferred being C14 to C18 fatty acids. The most preferred fatty acid is stearic acid. The fatty acid in the composition is more preferably present in an amount in the range of 5 to 20% by weight of the composition. Soaps in the vanishing cream base include alkali metal salt of fatty acids, like sodium or potassium salts, most preferred being potassium stearate. The soap in the vanishing cream base is generally present in an amount in the range of 0.1 to 10%, more preferably 0.1 to 3% by weight of the composition. Generally, the vanishing cream base in personal care compositions is prepared by taking a desired amount of total fatty matter and mixing with potassium hydroxide in desired amounts. The soap is usually formed insitu during the mixing.

An especially suitable cosmetically acceptable base is one which comprises a water-in-oil emulsion comprising silicone oils as the continuous phase. The water in oil emulsions preferably comprise a cross-linked silicone elastomer blend.

Inclusion of silicone elastomer blend in a water-in-oil emulsion may be used as the cosmetically acceptable base for preparing the compositions of the present invention. While silicone fluids may be used, silicone elastomers which are cross-linked, are especially preferred. The creation of cross-linkages between linear polymers, such as dimethicone, converts the linear polymer into a silicone elastomer. In contrast to silicone fluid polymers, the physical properties of elastomers are typically dependent on the number of cross-linkages, rather than molecular weight. The ability of silicone elastomers to swell makes them ideal thickeners for oil phases. The elastomers have a very smooth and soft feel when applied to skin or hair. They can also be used as delivery agents for fragrances, vitamins and other additives in cosmetic compositions.

Suitable silicone elastomer blends or gels which are commercially available and suitable for inclusion in the composition of the invention and found to provide the enhanced stability are: Dow Corning® EL-8051 IN Silicone Organic Elastomer Blend [INCI Name: Isodecyl Neopentanoate (and) Dimethicone/Bis Isobutyl PPG-20 Crosspolymer]; EL-8050 [INCI Name: Isododecane (and) Dimethicone/Bis-Isobutyl PPG 20 Crosspolymer] DC 9040, DC9041, DC9045 (Dimethicone crosspolymer); DC 9506, 9509 (Dimethicone vinyl dimethicone crosspolymer); Shin-Etsu KSG-15, KSG-16, KSG-17 (Dimethicone vinyl dimethicone crosspolymer). It is further preferred that the composition comprises 5 to 50% silicone elastomer by weight of the composition.

In the case of wash-off composition. In addition to the essential ingredients as described earlier, preferred embodiments of the cleansing compositions may also include other optional and preferred ingredients for their known benefits. The type and content will largely depend on the nature and type of cleansing composition as well as general principles of formulation science.

Preferably, the composition further comprises an additional surfactant selected from nonionic surfactant, cationic surfactant, amphoteric surfactants and mixtures thereof. In general, the surfactants may be chosen from the surfactants described in well-known textbooks like "Surface Active Agents" Vol. 1, by Schwartz & Perry, lnterscience 1949, Vol. 2 by Schwartz, Perry & Berch, lnterscience 1958, and/or the current edition of "McCutcheon's Emulsifiers and Detergents" published by Manufacturing Confectioners Company or in "Tenside-Taschenbuch", H. Stache, 2nd Edn., Carl Hauser Verlag, 1981.

Preferred nonionic surfactants are those with a C10-C20 fatty alcohol or acid hydrophobe condensed with from 2 to 100 moles of ethylene oxide or propylene oxide per mole of hydrophobe, C2-C10 alkyl phenols condensed with from 2 to 20 moles of alkylene oxide, mono- and di-fatty acid esters of ethylene glycol, fatty acid monoglyceride, sorbitan mono- and di-C8-C20 fatty acids, block copolymers (ethylene oxide/propylene oxide), polyoxyethylene sorbitan and mixtures thereof. Alkyl polyglycosides and saccharide fatty amides (e.g. methyl gluconamides) are also suitable nonionic surfactants.

Examples of suitable cationic detergent surfactant include cetyl trimethylammonium bromide, benzalkonium halides that are also known as alkyldimethylbenzylammonium halides. Preferred cationic surfactant that may be used in the composition is benzalkonium chloride, also known as alkyldimethylbenzylammonium chloride (or ADBAC).

Examples of suitable amphoteric detergent surfactant include amide, betaine and amine oxide type. Particular examples of amphoteric detergent surfactants include cocodiethanol amide and cocomonoethanol amide, cocoamidopropyl betaine and coco amido propyl amine oxide. A preferred amphoteric detergent surfactant that may be used as detergent surfactant in the composition is cocoamidopropyl betaine.

When incorporated the antimicrobial composition comprises from 1 to 80%, preferably from 5 to 75%, more preferably from 10 to 70% and even more preferably from 15 to 65% by weight of one or more of these additional surfactants selected from nonionic surfactant, cationic surfactant, amphoteric surfactants and mixtures thereof.

When the product is in the solid form for hard surface cleaning applications, surfactants are preferably selected from primary alkyl sulphate, secondary alkyl sulphonates, alkyl benzene sulphonates, or ethoxylated alkyl sulphates.

The antimicrobial composition of the invention is useful in oral care compositions e.g. in a dentifrice/toothpaste or oral rinse product. In such applications, preferred surfactants are anionic, nonionic or amphoteric in nature, preferably anionic or amphoteric.

The antimicrobial composition may be in form of a solid, a liquid, a gel or a paste. A person skilled in the art can prepare compositions in various formats by choosing one or more carrier materials and/or surfactant. The antimicrobial compositions of the present invention are useful for cleansing and care, in particular for skin cleansing and skin care. It is envisaged that the antimicrobial composition can be used as a leave-on product or a wash-off product, preferably a leave-on product. The antimicrobial composition of the present invention can also be used for cleansing and care of hard surfaces such as glass, metal, plastic and the like. The antimicrobial composition may be in the form of an antimicrobial wipe. By wipe is it meant a disposable substrate such as a porous or absorbent sheet or cloth which has been pre-treated with the composition comprising the acid and the polymer of the invention (as defined above) so as to incorporate the composition of the invention into or onto the substrate prior to its use by a consumer.

Water soluble/dispersible polymers is an optional ingredient that is highly preferred to be included in composition. These polymers can be cationic, anionic, amphoteric or nonionic types with molecular weights higher than 100,000 Dalton. They are known to increase the viscosity and stability of liquid cleanser compositions, to enhance in-use and after-use skin sensory feels, and to enhance lather creaminess and lather stability. Amount of the polymers, when present, may range from 0.1 to 10% by weight of the composition.

Examples of water soluble/or dispersible polymers include the carbohydrate gums such as cellulose gum, microcrystalline cellulose, cellulose gel, hydroxyethyl cellulose, hydroxypropyl cellulose, sodium carboxymethylcellulose, methyl cellulose, ethyl cellulose, guar gum, gum karaya, gum tragacanth, gum arabic, gum acacia, gum agar, xanthan gum and mixtures thereof; modified and nonmodified starch granules and pregelatinized cold water soluble starch; emulsion polymers such as Aculyn® 28, Aculyn® 22 or Carbopol® Aqua SF1; cationic polymer such as modified polysaccharides including cationic guar available from Rhone Poulenc under the trade name Jaguar® C13S, Jaguar® C14S, Jaguar® C17, or Jaguar® C16; cationic modified cellulose such as UCARE® Polymer JR 30 or JR 40 from Amerchol; N-Hance® 3000, N-Hance® 3196, N-Hance® GPX 215 or N-Hance® GPX 196 from Hercules; synthetic cationic polymer such as Merquat® 100, Merquat® 280, Merquat® 281 and Merquat® 550 sold by Nalco; cationic starches such as StaLok® 100, 200, 300 and 400 sold by Staley Inc.; cationic galactomannans such as Galactasol® 800 series by Henkel, Inc.; Quadrosoft® LM-200; and Polyquaternium-24®. Also suitable are high molecular weight polyethylene glycols such as Polyox® WSR-205 (PEG 14M), Polyox® WSR-N-60K (PEG 45), and Polyox® WSR-301 (PEG 90M).

The composition of the invention may additionally comprise a skin-lightening agent. Apart from niacinamide which is anyway presence as one of the essential component of the present composition, other well known skin lightening agents e.g. aloe extract, ammonium lactate, arbutin, azelaic acid, kojic acid, butyl hydroxy anisole, butyl hydroxy toluene, citrate esters, 3 diphenyl propane derivatives, 2, 5 dihydroxybenzoic acid and its derivatives, ellagic acid, fennel extract, gluco pyranosyl-1-ascorbate, gluconic acid, glycolic acid, green tea extract, hydroquinone, 4 hydroxyanisole and its derivatives, 4-hydroxy benzoic acid derivatives, hydroxycaprylic acid, lemon extract, linoleic acid, magnesium ascorbyl phosphate, mulberry root extract, 2,4 resorcinol derivatives, 3,5 resorcinol derivatives, salicylic acid, vitamins like vitamin B6, vitamin B12, vitamin C, vitamin A, a dicarboxylic acid, resorcinol derivatives, hydroxycarboxylic acid like lactic acid and their salts e.g. sodium lactate, and mixtures thereof.

Preferably, the composition may have sunscreen. Any sunscreen that can be suitably used with the base may be added. Both, UVA and UVB sunscreens may preferably be added.

The composition of the invention preferably comprises a UV-A sunscreen which is a dibenzoylmethane or its derivatives. Preferred dibenzoylmethane derivatives are selected from 4-tert-butyl-4'-methoxydibenzoylmethane, 2-methyldibenzoylmethane, 4-methyl-dibenzoylmethane, 4-isopropyldibenzoyl-methane, 4-tert-butyldibenzoylmethane, 2,4-dimethyldibenzoylmethane, 2,5-dimethyldibenzoylmethane, 4,4'-diisopropyl-dibenzoylmethane, 2-methyl-5-isopropyl-4'-methoxydibenzoylmethane, 2-methyl-5-tert-butyl-4'-methoxy-dibenzoyl methane, 2,4-dimethyl-4'-methoxy dibenzoylmethane or 2,6-dimethyl-4-tert-butyl-4'-methoxydibenzoylmethane. The most preferred dibenzoylmethane derivative is 4-tert-butyl-4'-methoxydibenzoylmethane. The composition of the invention preferably comprises 0.1 to 10%, more preferably 0.2 to 5%, further more preferably 0.4 to 3%, by weight dibenzoylmethane or a derivative thereof based on total weight of the composition and including all ranges subsumed therein.

The composition preferably comprises a UV-B organic sunscreen selected from the class of cinnamic acid, salicylic acid, diphenyl acrylic acid and derivatives thereof. Illustrative non-limiting example of UV-B sunscreens which are commercially available and useful for inclusion in the composition of the invention are Octisalate™, Homosalate™, NeoHelipan™, Octocrylene™, Oxybenzone™ or Parsol MCX™. The UV-B sunscreen is most preferably 2-ethyl-hexyl-4-methoxy cinnamate which is commercially available as Parsol MCX. The UV-B organic sunscreen is preferably included in 0.1 to 10%, more preferably 0.1 to 7% by weight of the composition. It has been observed that presence of an organic UV-B sunscreen like 2-ethyl-hexyl-4-methoxy cinnamate causes further rapid degradation of the UV-A dibenzoylmethane sunscreen in the presence of UV radiation. The presence of the rosmarinic acid ester compound is found to be very efficacious in stabilizing the composition even when UV-B sunscreens are present.

Useful inorganic sun-blocks are also preferably used in the present invention. These include, for example, zinc oxide, iron oxide, silica, such as fumed silica, and titanium dioxide.

Preservatives can also be added into the compositions to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Particularly preferred preservatives are phenoxyethanol, methyl paraben, propyl paraben, imidazolidinyl urea, sodium dehydroacetate and benzyl alcohol. The preservatives should be selected having regard for the use of the composition and possible incompatibility between the preservatives and other ingredients. Preservatives are preferably employed in amounts ranging from 0.01% to 2% by weight of the composition.

A variety of other optional materials may be formulated into the compositions. These may include: antimicrobials such as 2-hydroxy-4,2',4'-trichlorodiphenylether (triclosan), 2,6-dimethyl-4-hydroxychlorobenzene, and 3,4,4'-trichlorocarbanilide; scrub and exfoliating particles such as polyethylene and silica or alumina; cooling agents such as menthol; skin calming agents such as aloe vera; and colorants.

In addition, the compositions may further include 0 to 10% by weight of opacifiers and pearlizers such as ethylene glycol distearate, titanium dioxide or Lytron® 621 (Styrene/Acrylate copolymer); all of which are useful in enhancing the appearance or properties of the product.

Diluents other than water can include liquid or solid emollients, solvents, humectants, thickeners and powders. Examples of each of these types of vehicle, which can be used singly or as mixtures of one or more vehicles, are as follows:

Emollients, such as stearyl alcohol, glyceryl monoricinoleate, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, eicosanyl alcohol, behenyl alcohol, cetyl palmitate, silicone oils such as dimethylpolysiloxane, di-n-butyl sebacate, isopropyl myristate, isopropyl palmitate, isopropyl stearate, butyl stearate, polyethylene glycol, triethylene glycol, lanolin, cocoa butter, corn oil, cotton seed oil, olive oil, palm kernel oil, rape seed oil, safflower seed oil, evening primrose oil, soybean oil, sunflower seed oil, avocado oil, sesame seed oil, coconut oil, arachis oil, castor oil, acetylated lanolin alcohols, petroleum jelly, mineral oil, butyl myristate, isostearic acid, palmitic acid, isopropyl linoleate, lauryl lactate, myristyl lactate, decyl oleate, myristyl myristate;

Solvents, such as ethyl alcohol, isopropanol, acetone, ethylene glycol monoethyl ether, diethylene glycol monobutyl ether, diethylene glycol monoethyl ether;

In case of soap bars, it may contain particles that are greater than 50 µm in average diameter that help remove dry skin. Not being bound by theory, the degree of exfoliation depends on the size and morphology of the particles. Large and rough particles are usually very harsh and irritating. Very small particles may not serve as effective exfoliants. Such exfoliants used in the art include natural minerals such as silica, talc, calcite, pumice, tricalcium phosphate; seeds such as rice, apricot seeds, etc.; crushed shells such as almond and walnut shells; oatmeal; polymers such as polyethylene and polypropylene beads, flower petals and leaves; microcrystalline wax beads; jojoba ester beads, and the like. These exfoliants come in a variety of particle sizes and morphology ranging from micron sized to a few mm. They also have a range of hardness. Some examples are talc, calcite, pumice, walnut shells, dolomite and polyethylene.

Advantageously, active agents other than skin conditioning agents defined above may be added to the composition. These active ingredients may be advantageously selected from bactericides, vitamins, anti-acne actives; anti-wrinkle, anti-skin atrophy and skin repair actives; skin barrier repair actives; non-steroidal cosmetic soothing actives; artificial tanning agents and accelerators; skin lightening actives; sunscreen actives; sebum stimulators; sebum inhibitors; anti-oxidants; protease inhibitors; skin tightening agents; anti-itch ingredients; hair growth inhibitors; 5-alpha reductase inhibitors; desquamating enzyme enhancers; antiglycation agents; or mixtures thereof; and the like.

These active agents may be selected from water-soluble active agents, oil soluble active agents, pharmaceutically acceptable salts and mixtures thereof. The term "active agent" as used herein, means personal care actives which can be used to deliver a benefit to the skin and/or hair and which generally are not used to confer a skin conditioning benefit, such are delivered by emollients as defined above. The term "safe and effective amount" as used herein, means an amount of active agent high enough to modify the condition to be treated or to deliver the desired skin care benefit, but low enough to avoid serious side effects. The term "benefit," as used herein, means the therapeutic, prophylactic, and/or chronic benefits associated with treating a particular condition with one or more of the active agents described herein. What is a safe and effective amount of the active agent(s) will vary with the specific active agent, the ability of the active to penetrate through the skin, the age, health condition, and skin condition of the user, and other like factors.

Powders, such as chalk, talc, fullers earth, kaolin, starch, gums, colloidal silica sodium polyacrylate, tetra alkyl and/or trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, ethylene glycol monostearate.

The cosmetically acceptable base is usually from 10 to 99.9%, preferably from 50 to 99% by weight of the composition, and can, in the absence of other personal care adjuncts, form the balance of the composition.

The composition of the invention may comprise a conventional deodorant base as the cosmetically acceptable carrier. By a deodorant is meant a product in the stick, roll-on, or propellant medium which is used for personal deodorant benefit e.g. application in the under-arm area which may or may not contain anti-perspirant actives.

Deodorant compositions can generally be in the form of firm solids, soft solids, gels, creams, and liquids and are dispensed using applicators appropriate to the physical characteristics of the composition. Deodorant compositions which are delivered through roll-ons generally comprise a liquid carrier. Such liquid carrier can be hydrophobic or comprise a mixture of both hydrophilic and hydrophobic liquids. They may be in the form of an emulsion or a microemulsion. The liquid carrier or mixture of carriers often constitutes from 30 to 95% by weight of the composition and in many instances from 40 to 80%. Hydrophobic liquid carriers commonly can comprise one or more materials selected within the chemical classes of siloxanes, hydrocarbons, branched aliphatic alcohols, esters and ethers that have a melting point not higher than 25° C. and a boiling point of at least 100° C. Hydrophilic carrier liquids that can be employed in compositions herein commonly comprise water and/or a mono or polyhydric alcohol or water-miscible homologue. Monohydric alcohols often are short chain, by which is meant that they contain up to 6 carbons, and in practice is most often ethanol or sometimes iso-propanol. Polyhydric alcohols commonly comprise ethylene or propylene glycol, or a homologue can be employed such as diethylene glycol. Other than this suitable other vehicle and component used for deodorant composition can be added.

Preferably, when the composition is in the form of a hand sanitizer composition the cosmetically acceptable base may comprises of alcohol and water. The most preferred alcohols are ethyl alcohol and isopropyl alcohol. Even a mixture of two or more alcohol can preferably be used in the hand sanitizer composition. The amount of alcohol preferably in the range of 50 to 95%, more preferably 60 to 80% and most preferably 65 to 80% by weight of the hand sanitizer composition.

The compositions of the present invention can comprise a wide range of other optional components. The CTFA Personal care Ingredient Handbook, Second Edition, 1992, which is incorporated by reference herein in its entirety, describes a wide variety of non-limiting personal care and pharmaceutical ingredients commonly used in the skin care industry, which are suitable for use in the compositions of the present invention. Examples include: antioxidants, binders, biological additives, buffering agents, colorants, thickeners, polymers, astringents, fragrance, humectants, opacifying agents, conditioners, pH adjusters, natural extracts, essential oils, skin sensates, skin soothing agents, and skin healing agents.

The present invention also discloses a method of cleaning or disinfecting a surface comprising the steps of applying a composition according to the invention on to said surface in case of a leave-on composition. This method optionally comprises an additional step of at least partially removing the composition from the surface if it is in the form of a wash-off composition. Preferably, the step of at least partially removing the composition is carried out less than 5 minutes after the step of applying the composition on the substrate.

The present invention also discloses a use of a composition of the present invention as disclosed above for antimicrobial benefit. Therefore the composition of the present invention able to provide prolonged/long-lasting antimicrobial benefits. The preferred intended use/method of the composition of the present invention is non-therapeutic and/or cosmetic.

The present invention also discloses a use of a composition of the present invention as disclosed above for hand hygiene.

The present invention also provides a use of a combination of (a) 0.01 to 10% by weight of a water soluble vinyl polymer comprising polyvinyl alcohol (b) 0.1 to 20% by weight of a carboxylic acid having pKa greater than 4.5 or its derivatives thereof; and (c) 1 to 80% by weight an anionic surfactant; wherein the pH of the composition is in the range of 4.5 to 6.5, in a composition for improved antimicrobial benefits.

The use is preferably non-therapeutic.

The invention is now described further with the help of non-limiting examples provided below.

EXAMPLES

Protocols:

All the compositions shown in examples below were prepared using amounts (in percentage by weight) of polymers and carboxylic acids as shown in respective examples and procedure as follows:

The polymer solutions were prepared separately at 2% concentration by dissolving it in distilled water using a magnetic stirrer. Any lower desired concentrations were achieved by further diluting it in distilled water. All the carboxylic acids were used from the original 100% stock and diluted in distilled water to get desired concentrations. Before carrying out the assay for antimicrobial efficacy using contact kill assay, pH of all the samples were adjusted to 5.2±0.2 using 0.1N sodium hydroxide or hydrochloric acid.

Assessment of Antimicrobial Efficacy:

Assessment of antimicrobial efficacy was carried out as per (American Standard Test Method 2783). The test organisms were grown on tryptic soya agar (TAS) plates overnight (22±2 h). The organisms were not more than 3 passages removed from the original source. The cell number was adjusted based on optical density (OD) of the cells by re-suspending it in a suitable amount of physiological saline sufficient to achieve the required cell number. The OD at 620 nm of the cells was standardized to a cell number for each test organism using a spectrophotometer. A minimum final suspension of 1×10⁹ colony forming units (CFU)/mL was achieved by adjusting the OD to 2.0 in saline for the contact kill assay.

In each test, 9.9 mL of a test sample was taken in 100 mL sample container. 0.1 mL of culture was added to the test samples at time zero and the timer was started within 1 second. The test solution was immediately vortexed upon addition of culture. At time point e.g. 10 seconds, 30 seconds and 60 seconds, 1.0 mL aliquot was removed from the tube and immediately transferred to a 9.0 mL neutralizer (D/E neutralizing broth from BD Difco reference number 281910) in a glass tube. Serial ten-fold dilutions of the neutralized samples were prepared using 9.0 mL dilution blanks and enumerated, in duplicate, using standard plating techniques (pour plate). The plating of all the samples were completed within 30 min of completing the neutralization step. The plates were incubated at 37 C for 24 to 48 h. The colonies were counted and the counts were converted to log values. The log reduction was calculated as:

$$Logic_{10}\ Reduction\ (LR) = Log_{10}\ of\ control - Log_{10}\ of\ test\ sample.$$

Log reduction greater than 5 means 99.99% reduction in the number of CFU and log reduction less than 0.5 means no reduction in the number of CFU that means no antimicrobial efficacy. Log reduction greater than 5 also denotes complete kill.

In a first set of experiments different water-soluble vinyl polymers has been tried either alone or with different carboxylic acids having pKa greater than 4.5 as per Table 1. The pKa values of different carboxylic acid that has been used in the experiments are as follows:

Octanoic acid—(pKa=4.89; from Aldrich, catalogue number O3907)
4-methyl octanoic acid—(pKa=4.93; from Aldrich, catalogue number W357502)
Hexanoic acid—(pKa=4.88; from Aldrich, catalogue number 153745)
2-ethyl hexanoic acid—(pKa=4.72; from Aldrich, catalogue number 538701)
Cyclohexanoic acid—(pKa=4.92; from Aldrich, catalogue number 101834)

TABLE 1

| Example No. | PVA | PVP | PAA | Octanoic acid | 4-methyl octanoic acid | Hexanoic acid | 2-ethyl hexanoic acid | Cyclohexanoic acid |
|---|---|---|---|---|---|---|---|---|
| A | 2 | — | — | — | — | — | — | — |
| B | — | 2 | — | — | — | — | — | — |
| C | — | — | 2 | — | — | — | — | — |
| D | — | — | — | 0.5 | — | — | — | — |
| E | — | — | — | — | 0.5 | — | — | — |
| F | — | — | — | — | — | 0.5 | — | — |
| G | — | — | — | — | — | — | 0.5 | — |
| H | — | — | — | — | — | — | — | 0.5 |
| I | — | 0.2 | — | 0.5 | — | — | — | — |
| J | — | — | 0.2 | 0.5 | — | — | — | — |
| 1 | 0.2 | — | — | 0.5 | — | — | — | — |
| 2 | 0.2 | — | — | — | 0.5 | — | — | — |
| 3 | 0.2 | — | — | — | — | 0.5 | — | — |
| 4 | 0.2 | — | — | — | — | — | 0.5 | — |
| 5 | 0.2 | — | — | — | — | — | — | 0.5 |

The above compositions were then tested for its antimicrobial efficacy using the protocol as discussed in the previous section. The results of the antimicrobial efficacy tasting is summarized below in Table 2:

TABLE 2

| | Log Reduction Value at 30 Seconds | |
|---|---|---|
| Example No. | For *E. coli* | For *S. aureus* |
| A | <0.5 | <0.5 |
| B | <0.5 | <0.5 |
| C | <0.5 | <0.5 |
| D | 0.6 ± 0.31 | 0.8 ± 26 |
| E | 0.5 ± 0.28 | 0.9 ± 0.37 |
| F | <0.5 | <0.5 |
| G | <0.5 | <0.5 |
| H | <0.5 | <0.5 |
| I | 1.8 ± 0.22 | 2.4 ± 0.15 |
| J | 2.0 ± 0.18 | 2.8 ± 0.11 |
| 1 | >5 | >5 |
| 2 | >5 | >5 |
| 3 | >5 | >5 |
| 4 | >5 | >5 |
| 5 | >5 | >5 |

From the above table it is evident that the compositions that are within the scope of the present invention (Example 1 to 5) provides complete kill (99.9%) hence the log reduction is greater than 5. However, the compositions that are outside the scope of the present invention (Example A to I) does not provide good antimicrobial efficacy. It can also be seen from the above table that PVA when used in combination with any of the carboxylic acids having pKa greater than 4.5 provides more than 5 log reduction (complete kill). PVA and the carboxylic acids thus exhibit synergistic antimicrobial efficacy. Importantly, such antimicrobial effect is obtained from relatively short contact time, i.e. 30 seconds.

In a second set of experiments, different carboxylic acid having pKa less than 4.5 (have been tested with PVA as per Table 3. The pKa values of these different carboxylic acids are as follows:

Benzoic acid—(pKa=4.2; from Merck, catalogue number MK4M542724)
Salicylic acid—(pKa=2.97 from Sigma Aldrich, catalogue number 247588)
Citric acid—(pKa=3.13 from Sigma Aldrich, catalogue number C83155)
Lactic acid—(pKa=3.86 from Sigma Aldrich, catalogue number 252476)
Malic acid—(pKa=3.4 from Sigma Aldrich, catalogue number M8304)
Glycolic acid—(pKa=3.6 from Sigma Aldrich, catalogue number V900017)

TABLE 3

| Example | K | L | M | N | O | P |
|---|---|---|---|---|---|---|
| PVA | 0.2 | 0.2 | 0.2 | 0.2 | 0.2 | 0.2 |
| Benzoic acid | 0.5 | — | — | — | — | — |
| Salicylic acid | — | 0.5 | — | — | — | — |
| Citric acid | — | — | 0.5 | — | — | — |
| Lactic acid | — | — | — | 0.5 | — | — |
| Malic acid | — | — | — | — | 0.5 | — |
| Glycolic acid | — | — | — | — | — | 0.5 |

The above compositions were then tested for its antimicrobial efficacy using the protocol as discussed in the previous section. The results of the antimicrobial efficacy tasting is summarized below in Table 4:

TABLE 4

| Example No. | Log Reduction Value at 30 Seconds | |
| --- | --- | --- |
| | For E. coli | For S.aureus |
| K | <0.5 | <0.5 |
| L | <0.5 | <0.5 |
| M | <0.5 | <0.5 |
| N | <0.5 | <0.5 |
| O | <0.5 | <0.5 |
| P | <0.5 | <0.5 |

As can be seen from the data in table 4, carboxylic acids having $pK_a$ less than 4.5, i.e. carboxylic acids outside the scope of the present invention, when used in combination with PVA, does not exhibits any antimicrobial efficacy.

In a third, set of experiments different polymers has been tested, other than water-soluble vinyl polymers, alone and in combination with a carboxylic acid having $pK_a$ greater than 4.5 as per the following Table 5. For this purpose the below mentioned polymers tested:
PVA—ALDRICH, catalogue number 363170,
PVP—from SIGMA-ALDRICH under name PVP10,
PAA—from ALDRICH, catalogue number 523925,
Polystyrene sulfonate (PSS)—from AkzoNobel sold under name FLEXAN® II,
Sodium carboxymethyl cellulose (SCMC)—from ALDRICH, catalogue number 419273,
Hydroxyethyl cellulose (HEC)—from SIGMA, catalogue number 09368; and
Na-Alginate—from Thomas Baker, catalogue number 142582.

TABLE 5

| | Example | | | | |
| --- | --- | --- | --- | --- | --- |
| | Q | R | S | T | U |
| PSS | — | 0.2 | — | — | — |
| SCMC | — | — | 0.2 | — | — |
| HEC | — | — | — | 0.2 | — |
| Sodium Alginate | — | — | — | — | 0.2 |
| Octanoic acid | 0.5 | 0.5 | 0.5 | 0.5 | 0.5 |

The above compositions were then tested for its antimicrobial efficacy using the protocol as discussed in the previous section. The results of the antimicrobial efficacy tasting is summarized below in Table 6:

TABLE 6

| Example No. | Log Reduction Value at 30 Seconds | |
| --- | --- | --- |
| | For E. coli | For S.aureus |
| Q | 0.7 ± 0.22 | 1.0 ± 0.23 |
| R | 3.3 ± 0.16 | 3.6 ± 0.22 |
| S | 1.5 ± 0.13 | 1.6 ± 0.24 |
| T | <0.5 | <0.5 |
| U | <0.5 | <0.5 |

As can be seen from data in table 6, polymers other than water soluble vinyl polymers when used in combination with octanoic acid (pKa greater than 4.5) does not provide the required antimicrobial efficacy in relatively short contact times like 30 seconds as that obtained when PVA was used in combination with octanoic acid (Example 1).

In a fourth set of experiments, carboxylic acid having pKa greater than 4.5 and PVA were combined in presence of anionic surfactants as per the following table 7. For this purpose, the anionic surfactants mentioned below were tested:
Sodium lauryl ether sulfate (SLES) catalogue number LES 70-SLES from Galaxy Surfactant Ltd; and
Sodium lauryl sulfate (SLS), catalogue number 62862 from Sigma-Aldrich.

TABLE 7

| Example | V | W | 6 | X | 7 | Y | Z | 8 | ZA | 9 |
| --- | --- | --- | --- | --- | --- | --- | --- | --- | --- | --- |
| Octanoic acid | 1 | 1 | 1 | 1 | 1 | — | — | — | — | — |
| Cyclohexanoic acid | — | — | — | — | — | 1 | 1 | 1 | 1 | 1 |
| SLES | — | 5 | 5 | — | — | — | 5 | 5 | — | — |
| SLS | — | — | — | 5 | 5 | — | — | — | 5 | 5 |
| PVA | — | — | 0.5 | — | 0.5 | — | — | 0.5 | — | 0.5 |

The above compositions were then tested for its antimicrobial efficacy using the protocol as discussed in the previous section. The results of the antimicrobial efficacy tasting is summarized below in Table 7:

TABLE 8

| Example No. | Log Reduction Value for E. coli | | |
| --- | --- | --- | --- |
| | 10 seconds | 30 seconds | 60 seconds |
| V | 4.2 ± 0.22 | >5 | >5 |
| W | 0.44 ± 0.19 | 0.71 ± 0.14 | 1.7 ± 0.13 |
| 6 | 1.9 ± 0.25 | 2.8 ± 0.21 | 3.9 ± 0.18 |
| X | 1.7 ± 0.18 | 2.5 ± 0.22 | 3.2 ± 0.11 |
| 7 | 2.7 ± 0.28 | 3.6 ± 0.25 | 4.8 ± 0.14 |
| Y | 4.1 ± 0.19 | >5 | >5 |
| Z | 0.32 ± 0.13 | 0.56 ± 0.12 | 1.3 ± 0.23 |
| 8 | 1.7 ± 0.21 | 2.4 ± 0.11 | 3.3 ± 0.16 |
| ZA | 1.4 ± 0.16 | 2.1 ± 0.21 | 2.9 ± 0.12 |
| 9 | 2.5 ± 0.12 | 3.3 ± 0.22 | 4.1 ± 0.13 |

As can be seen from the data in table 8 above, 1% of carboxylic acids having pKa greater than 4.5 alone, provided more than 5 log reduction in 30 seconds (examples V and Y). However, this antimicrobial effect delivered by carboxylic acid having pKa greater than 4.5 alone, was found to have drastically reduced in presence of anionic surfactants (examples W, X, Z and ZA) at all contact times tested, i.e. 10 seconds, 30 seconds and 60 seconds.

It is only when PVA was added, an improvement in antimicrobial effect was obtained as shown in examples 6 to 9 compared to that of control (examples W, X, Z and ZA, respectively). Moreover, this improved antimicrobial effect was obtained within the same relatively short contact time e.g. 10 seconds and 30 seconds which improved further by contact time of 60 seconds. Further, this improved antimicrobial effect was obtained in pH range 4.8±0.3.

Therefore, from the description and from the above examples it is clear that a synergistic antimicrobial benefit is obtained when water-soluble vinyl polymers comprising polyvinyl alcohol are used in combination with carboxylic acids having pKa greater than 4.5 in presence of an anionic surfactant. Moreover, such synergistic antimicrobial efficacy is obtained in relatively short contact times in absence of soap and at pH close to that of human skin.

The invention claimed is:

1. An antimicrobial composition comprising:
   a. 0.01 to 10% by weight of a water soluble vinyl polymer comprising polyvinyl alcohol; and
   b. 0.1 to 20% by weight of a carboxylic acid having pKa greater than 4.5;
   c. 1 to 80% by weight an anionic surfactant;
   d. 5 to 25% by weight fatty acids different from the carboxylic acid above; and
   e. 0.1 to 10% by weight soap
   wherein the pH of the composition is in the range of 5 to 6.5; and
   wherein the anionic surfactant is selected from sodium lauryl sulfate, sodium lauryl ether sulfate;
   wherein the composition has a log reduction of greater than 5 in the number of colony forming units;
   wherein the composition is a vanishing cream.

2. The antimicrobial composition according to claim 1, wherein the vinyl polymer is polyvinyl alcohol.

3. The antimicrobial composition according to claim 1, wherein the carboxylic acid is selected from aliphatic carboxylic acids having chain length C4 to C16.

4. The antimicrobial composition according to claim 3, wherein the aliphatic carboxylic acid is selected from linear or branched aliphatic carboxylic acids, cyclic aliphatic carboxylic acids and mixtures thereof.

5. The antimicrobial composition according to claim 4, wherein the aliphatic carboxylic acid is selected from hexanoic acid, cyclohexanoic acid, 2-ethyl hexanoic acid, octanoic acid, 4-methyl octanoic acid and mixtures thereof.

6. The antimicrobial composition according to claim 1 further comprising a cosmetically acceptable base.

7. A method of cleaning or disinfecting a surface comprising the step of applying the antimicrobial composition according to claim 1 on to a surface.

8. The method according to claim 7, wherein the antimicrobial composition is in the form of a wash-off composition and wherein there is an additional step of at least partially removing the applied composition.

9. The method according to claim 8, wherein the step of at least partially removing the antimicrobial composition is carried out in less than 5 minutes after the step of applying the composition on to the substrate.

10. A method for obtaining antimicrobial benefit comprising applying the antimicrobial composition according to claim 1 to surfaces of a human body.

11. A method of improving hand hygiene comprising washing hands with the antimicrobial composition according to claim 1.

12. The antimicrobial composition according to claim 1, wherein an antimicrobial effect is obtained from a contact time with a surface of 30 seconds.

13. The antimicrobial composition according to claim 12, wherein the contact time is 10 seconds.

14. The antimicrobial composition according to claim 1, wherein the composition is a sanitizer composition.

15. The antimicrobial composition according to claim 14, wherein the composition is a hand sanitizer.

16. The antimicrobial composition according to claim 1, wherein the fatty acid is C13 to C20 fatty acid.

17. The antimicrobial composition according to claim 1, wherein the composition comprises 0.1 to 3% by weight soap.

* * * * *